(12) United States Patent
Buehler et al.

(10) Patent No.: US 10,070,666 B2
(45) Date of Patent: Sep. 11, 2018

(54) NICOTINE POWDER DELIVERY SYSTEM WITH AIRFLOW MANAGEMENT MEANS

(71) Applicant: Philip Morris Products S.A., Neuchatel (CH)

(72) Inventors: Frederic Buehler, Neuchatel (CH); Robert Emmett, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 74 days.

(21) Appl. No.: 15/319,981

(22) PCT Filed: Jun. 19, 2015

(86) PCT No.: PCT/EP2015/063878
§ 371 (c)(1),
(2) Date: Dec. 19, 2016

(87) PCT Pub. No.: WO2015/193498
PCT Pub. Date: Dec. 23, 2015

(65) Prior Publication Data
US 2017/0135397 A1  May 18, 2017

(30) Foreign Application Priority Data

Jun. 20, 2014  (EP) .................................. 14173343

(51) Int. Cl.
*A24F 47/00* (2006.01)
*A61M 15/00* (2006.01)

(52) U.S. Cl.
CPC ....... *A24F 47/002* (2013.01); *A61M 15/0035* (2014.02)

(58) Field of Classification Search
CPC ............ A61M 15/0028; A61M 15/003; A61M 15/0031; A61M 15/0033; A61M 15/0035;
(Continued)

(56) References Cited

U.S. PATENT DOCUMENTS 3,596,663 A   8/1971  Schultz et al.
4,553,556 A  11/1985  Lephardt
(Continued)

FOREIGN PATENT DOCUMENTS

EP   0 160 380 A1  11/1985
EP   0 940 354 A1   9/1999

OTHER PUBLICATIONS

International Search Report and Written Opinion dated Jul. 31, 2015 in PCT/EP2015/063878 filed Jun. 19, 2015.

*Primary Examiner* — Eric Yaary
(74) *Attorney, Agent, or Firm* — Oblon, McClelland, Maier & Neustadt, L.L.P.

(57) ABSTRACT

An aerosol-generating article is provided, including a nicotine powder receptacle containing a dose of nicotine powder; a corrugated inner wrapper wrapped around the nicotine powder receptacle; an outer wrapper wrapped around the corrugated inner wrapper; at least one airflow inlet upstream of the nicotine powder receptacle; and at least one airflow outlet downstream of the nicotine powder receptacle, wherein corrugations in the corrugated inner wrapper define a plurality of airflow channels in fluid communication with the at least one airflow inlet and the at least one airflow outlet.

15 Claims, 1 Drawing Sheet

(58) Field of Classification Search
CPC .......... A61M 15/0036; A61M 15/0038; A61M 15/004; A61M 15/0041
See application file for complete search history.

(56) References Cited

U.S. PATENT DOCUMENTS

| | | |
|---|---|---|
| 5,178,166 A | 1/1993 | Newsome et al. |
| 5,441,060 A | 8/1995 | Rose et al. |
| 5,687,746 A | 11/1997 | Rose et al. |
| 5,746,227 A | 5/1998 | Rose et al. |
| 6,595,209 B1 | 7/2003 | Rose et al. |
| 2011/0220106 A1* | 9/2011 | Ganem ............. A61M 15/0028 128/203.21 |
| 2012/0060855 A1* | 3/2012 | Fiebelkorn ............. A24D 3/043 131/336 |
| 2014/0026900 A1 | 1/2014 | Karles et al. |

* cited by examiner

NICOTINE POWDER DELIVERY SYSTEM WITH AIRFLOW MANAGEMENT MEANS

The present invention relates to an article comprising nicotine powder. The invention further relates to a nicotine powder delivery system comprising said article and a device configured to receive and cooperate with the article to deliver nicotine to a user.

Dry powder inhalers are known in the art and may be used, for example to treat respiratory diseases by delivering a dry powder comprising a pharmaceutical in aerosol form to a patient's airways.

It is an object of the present invention to provide an article suitable for delivering a nicotine powder to a user. Advantageously, such an article provides a sufficiently high airflow rate for the effective delivery of nicotine powder to a user.

It is another objective of the present invention to provide a nicotine powder delivery system comprising a re-usable device suitable for engaging and interacting with the article to provide nicotine powder to a user.

In one aspect, the present invention provides an aerosol-generating article comprising a nicotine powder receptacle containing a dose of nicotine powder, a corrugated inner wrapper wrapped around the nicotine powder receptacle, and an outer wrapper wrapped around the corrugated inner wrapper. The article comprises at least one airflow inlet upstream of the nicotine powder receptacle, at least one airflow outlet downstream of the nicotine powder receptacle, and the corrugations in the corrugated inner wrapper define a plurality of airflow channels in fluid communication with the at least one airflow inlet and the at least one airflow outlet.

As used herein, the term "corrugated" is used to describe a wrapper having a series of alternating troughs and ridges. The troughs and ridges may follow any path, such as a straight line and can extend across the inner wrapper at any angle. At least two lines of corrugations may meet to form a chevron. The corrugations may extend over all or a part of the inner wrapper. The cross sectional profile of the corrugations may follow any desired shape, such as a sine wave or a saw tooth profile.

As used herein, the term "airflow inlet" is used to describe one or more apertures through which air may be drawn into the aerosol-generating article according to the invention. Similarly, the term "airflow outlet" is used to describe one or more apertures through which air may be drawn out of the aerosol-generating article according to the invention.

As used herein, the terms "upstream" and "downstream" are used to describe the relative positions of components, or portions of components, of aerosol-generating articles according to the invention with respect to the direction of airflow through the aerosol-generating article when a user draws on the aerosol-generating article. In particular, when a user draws on the article, air flows in the downstream direction from the at least one airflow inlet to the at least one airflow outlet.

Providing a corrugated inner wrapper between the nicotine powder receptacle and the outer wrapper advantageously forms a plurality of airflow channels around the outside of the receptacle. Advantageously, the plurality of airflow channels in fluid communication with the at least one airflow inlet and the at least one airflow outlet optimises the airflow through the article. As compared to an article without the corrugated inner wrapper, the wrapper reduces the resistance to draw when a user draws air through the article. This increases the airflow rate and can facilitate effective delivery of the nicotine powder to the user.

Providing airflow channels using a corrugated inner wrapper also facilitates simple, cost effective manufacture of the aerosol-generating article according to the invention by allowing manufacture using existing combining technology and machinery. In particular, the article can be assembled by wrapping the corrugated inner wrapper around the nicotine powder receptacle and then wrapping the outer wrapper around the inner wrapper. This method of construction is faster and easier to implement than alternative methods, for example a method involving insertion of the receptacle into a pre-formed tube.

As defined herein, a nicotine powder receptacle is a container housing nicotine powder. Preferably, the receptacle is filled with nicotine powder. The nicotine powder may be blended with additional suitable ingredients, for example suitable ingredients in powder form.

The corrugated inner wrapper is preferably formed from a corrugated paper, which is cost effective and can be readily integrated into existing manufacture processes that are already adapted to handle paper materials when forming wrappers.

To provide sufficient rigidity to the corrugations and prevent collapse of the plurality of airflow passages during manufacture and subsequent handling of the article of the invention, the corrugated paper may have a basis weight of at least about 70 grams per square meter, optionally at least about 100 grams per square meter, optionally at least about 115 grams per square meter. Basis weight of the paper is measured when the paper is flat, that is without corrugations.

Additionally, or alternatively, the corrugated paper may have a caliper of at least about 100 micrometers, optionally at least about 120 micrometers, optionally at least about 140 micrometers.

To facilitate bending of the corrugated paper when wrapping the corrugated paper around the nicotine powder receptacle to form the corrugated inner wrapper, the corrugated paper may have a basis weight of less than about 150 grams per square meter, optionally less than about 115 grams per square meter, optionally less than about 100 grams per square meter.

Additionally, or alternatively, the corrugated paper may have a caliper of less than about 200 micrometers, optionally less than about 140 micrometers, optionally less than about 120 micrometers.

Additionally, or alternatively, the corrugated inner wrapper may be formed from a high-stretch paper that exhibits a stretch of between about 15 percent and about 20 percent.

In some embodiments, the nicotine powder receptacle may comprise a capsule, preferably a breakable capsule that can be readily ruptured by a user prior to use of the article. For example, the capsule may be ruptured by the user squeezing the article about the capsule. Alternatively, the capsule may be ruptured by inserting the article into a device having a rupturing or piercing member, as described in more detail below. Providing the nicotine powder in a breakable capsule advantageously seals and isolates the nicotine powder, and therefore prevents deterioration or contamination of the powder prior to use of the article according to the invention.

Suitable materials for forming such capsules include, for example, gelatine, hydroxy propyl methyl cellulose, polyethylene, polypropylene, polyurethane, fluorinated ethylene propylene, and combinations thereof.

In certain preferred embodiments, the capsule may be formed from one or more biodegradable polymeric materials. This may advantageously reduce the environmental impact of aerosol-generating articles according to the invention.

The capsule may have any suitable size or shape. For example, the capsule may be cylindrical.

The capsule may have a length of, for example, between about 4 mm and about 12 mm. In certain preferred embodiments, the capsule has a length of about 8 mm.

The capsule may have a diameter or a width of, for example, between about 4 mm and about 10 mm. In certain preferred embodiments, the capsule has a diameter or a width of about 7 mm.

The capsule may have a thickness of, for example, between about 0.1 mm and about 1.0 mm. In certain preferred embodiments, the capsule has a thickness of between about 0.2 mm and about 0.4 mm.

The capsule in which the nicotine powder is encapsulated may be formed from one or more nicotine-resistant polymeric materials.

Alternatively or in addition, the interior of the capsule in which the nicotine powder is encapsulated may be coated with one or more nicotine-resistant polymeric materials.

In such embodiments, the nicotine-resistant polymeric coating on the interior of the capsule in which the nicotine powder is encapsulated may have a thickness of, for example, between about 5 μm and about 100 μm. In certain preferred embodiments, the nicotine-resistant polymeric coating on the interior of the capsule in which the nicotine powder is encapsulated has a thickness of about 40 μm.

Examples of suitable nicotine-resistant polymeric materials include, but are not limited to, polyethylene, polypropylene, polystyrene, fluorinated ethylene propylene, polytetrafluoroethylene, epoxy resins, polyurethane resins, vinyl resins and combinations thereof.

Use of one or more nicotine-resistant polymeric materials to form or coat the interior of the capsule in which the nicotine powder is encapsulated may advantageously enhance the shelf life of aerosol-generating articles according to the invention.

In those embodiments in which the capsule is intended to be broken using a squeezing action, the breakable capsule is preferably breakable under a crushing force of less than about 50 Newtons, optionally less than about 10 Newtons, optionally less than about 5 Newtons. Providing a capsule that breaks at a crushing force within these ranges ensures that it is relatively easy for the user to crush the capsule by hand.

Additionally, or alternatively, breaking the breakable capsule may require a crushing force of at least about 3 Newtons, optionally at least about 5 Newtons, optionally at least about 10 Newtons. Providing a capsule that requires a minimum breaking force within these ranges reduces the risk of accidental rupturing of the capsule during manufacture and subsequent handling of the article prior to use.

Unless otherwise specified, the crushing force required to break a breakable capsule is measured in accordance with ASTM D6175.

Advantageously, the nicotine powder may be a nicotine salt or nicotine salt hydrate. Suitable nicotine salts or nicotine salt hydrates include, for example, nicotine tartrate, nicotine aspartate, nicotine lactate, nicotine glutamate, nicotine bitartrate, nicotine salicylate, nicotine fumarate, nicotine mono-pyruvate, nicotine hydrochloride, and combinations thereof.

The nicotine powder may have any suitable particle size distribution for pulmonary delivery of the nicotine to a user. In certain embodiments of the invention, at least about 90 weight percent (wt %) of the nicotine powder may have a particle size of about 10 micrometers or less, preferably about 7 micrometers or less. The nicotine powder preferably has a mean average diameter ranging from about 0.1 to about 10 micrometers, more preferably from about 1 to about 7 micrometers, particularly preferably from about 2 to 6 about micrometers.

The nicotine powder particles for use in an aerosol-generating article according to the invention may be surface modified, for example the nicotine salt particles may be coated. A preferred coating material is L-leucine. These carrier-free nicotine powders are known in the art and available from Teicos Pharma Inc., Espoo, Finland. Particularly suitable nicotine powder particles include L-leucine coated nicotine bitartrate, L-leucine coated nicotine glutamate and L-leucine coated asparate.

The nicotine powder receptacle preferably contains between about 5 and about 20 milligrams of nicotine powder. In a particularly preferred embodiment, the nicotine powder receptacle contains about 10 milligrams of nicotine powder. The nicotine powder receptacle preferably contains sufficient nicotine powder to deliver between about 10 and about 30 puffs to a user.

The aerosol-generating article according to the invention may further comprise a flavour delivery element for providing a flavour sensation to a user when the user draws air through the article.

The flavour delivery element is preferably provided in series with the nicotine powder receptacle to minimise the impact on the external diameter or width of the article.

Preferably, the aerosol-generating article according to the invention is an elongate stick-like article with dimensions similar or identical to those of a conventional lit end cigarette.

As used herein, by "in series" it is meant that the flavour delivery element and the nicotine powder receptacle are arranged within the article so that in use an air stream drawn through the article passes through or around one of the flavour delivery element and the nicotine powder receptacle and then passes through or around the other of the flavour delivery element and the nicotine powder receptacle.

Preferably, the flavour delivery element is provided upstream of the nicotine powder receptacle so that the flavour delivery element does not obstruct the delivery of the nicotine powder from the nicotine powder receptacle to the user. In this case, the plurality of airflow passages advantageously direct airflow from the flavour delivery element around the outside of the nicotine powder receptacle so that sufficient flavour is delivered to the user despite the flavour delivery element being upstream of the nicotine powder receptacle.

To prevent leakage of a flavourant from the flavour delivery element the flavour delivery element preferably comprises a breakable capsule that may be ruptured by a user squeezing the article about the capsule.

Suitable materials for forming a breakable capsule providing a flavour delivery element include, for example, gel forming agents and hydrocolloids such as xanthan gum, gellan gum, carboxymethyl cellulose, carbopol, araboxymethyl cellulose, and combinations thereof.

The breakable capsule is preferably breakable under a crushing force of less than about 50 Newtons, optionally less than about 10 Newtons, optionally less than about 5 Newtons. Providing a capsule that breaks at a crushing force within these ranges ensures that it is relatively easy for the user to crush the capsule by hand.

Additionally, or alternatively, breaking the breakable capsule may require a crushing force of at least about 3 Newtons, optionally at least about 5 Newtons, optionally at least about 10 Newtons. Providing a capsule that requires a minimum breaking force within these ranges reduces the risk of accidental rupturing of the capsule during manufacture and subsequent handling of the article prior to use.

Alternatively or in addition to a breakable capsule, the flavour delivery element may be a carrier element, such as a thread, impregnated with a flavourant. Preferably, the flavourant in these embodiments is menthol. The thread can be disposed in a filter element that is preferably upstream of the nicotine powder receptacle.

The filter element containing the flavour delivery element may be formed of a suitable material known in the art such as cellulose acetate tow. The filter element may comprise a plug of filtering material wrapped in paper or plug wrap. The filtering material may be upstream or downstream of the flavour delivery element, preferably the filtering material is disposed both upstream and downstream of the flavour delivery element. In some embodiments of the invention, the flavour delivery element may extend through the filtering material. Preferably, the filter element has a low or very low particulate filtration efficiency and is designed such that it does not adversely impact delivery of the nicotine powder.

In any of the embodiments comprising a flavour delivery element, the flavour delivery element comprises one or more flavourants that may be in the form of a liquid or a solid (at room temperature of about 22 degrees Celsius and one atmosphere pressure). Solid flavourants may be in the form of a powder.

Flavourants can include flavour formulations, flavour-containing materials and flavour precursors. The flavourant may include one or more natural flavourants, one or more synthetic flavourants, or a combination of natural and synthetic flavourants.

Flavourants refers to a variety of flavour materials of natural or synthetic origin. They include single compounds and mixtures. Preferably the flavourant has flavour properties that enhance the experience of the nicotine powder inhalation article to, for example, provide an experience similar to that resulting from smoking a combustible smoking article. For example, the flavourant can enhance flavour properties such as mouth fullness and complexity. Complexity is generally known as the overall balance of the flavour being richer without dominating single sensory attributes. Mouth fullness is described as perception of richness and volume in the mouth and throat of the consumer.

Suitable flavours and aromas include, but are not limited to, any natural or synthetic flavour or aroma, such as tobacco, smoke, menthol, mint (such as peppermint and spearmint), chocolate, licorice, citrus and other fruit flavours, gamma octalactone, vanillin, ethyl vanillin, breath freshener flavours, spice flavours such as cinnamon, methyl salicylate, linalool, bergamot oil, geranium oil, lemon oil, and ginger oil, and the like.

Other suitable flavours and aromas may include flavour compounds selected from the group consisting of an acid, an alcohol, an ester, an aldehyde, a ketone, a pyrazine, combinations or blends thereof and the like. Suitable flavour compounds may be selected, for example, from the group consisting of phenylacetic acid, solanone, megastigmatrienone, 2-heptanone, benzylalcohol, cis-3-hexenyl acetate, valeric acid, valeric aldehyde, ester, terpene, sesquiterpene, nootkatone, maltol, damascenone, pyrazine, lactone, anethole, iso-s valeric acid, combinations thereof, and the like.

In some embodiments, the flavourant is a high potency flavourant, and is typically used at levels that would result in less than 200 parts per million in inhalation air flow. Examples of such flavourants are key tobacco aroma compounds such as beta-damascenone, 2-ethyl-3,5-dimethyl-pyrazine, phenylacetaldehyde, guaiacol, and furaneol. Other flavourants can only be sensed by humans at higher concentration levels. These flavourants, which are referred to herein as the low potency flavourants, are typically used at levels that results in orders of magnitude higher amounts of flavourant released into the inhalation air. Suitable low potency flavourants include, but are not limited to, natural or synthetic menthol, peppermint, spearmint, coffee, tea, spices (such as cinnamon, clove and ginger), cocoa, vanilla, fruit flavours, chocolate, eucalyptus, geranium, eugenol and linalool.

The article according to the invention may have a length of between about 40 and about 60 millimeters. In a particularly preferred embodiment, the article according to the invention has a length of about 50 millimeters.

The article according to the invention may have an outer diameter of between about 7 and about 10 millimeters. In a particularly preferred embodiment, the article has an outer diameter of about 8 millimeters.

In some embodiments, the nicotine powder inhalation article may used as such, that is as a stand-alone article, particularly in those embodiments in which the nicotine powder receptacle comprises a breakable capsule designed to be broken by the user squeezing the capsule. However, to facilitate consistent and reliable use and nicotine delivery, the aerosol-generating article of the invention is preferably combined with a device to form a nicotine powder delivery system.

Accordingly, the present invention also provides a nicotine powder delivery system comprising an aerosol-generating article in accordance with any of the embodiments described herein and a nicotine powder delivery device configured to receive such an article. Such a device is designed to effectively cooperate with the article according to the invention to deliver nicotine to the user. The device comprises an outer housing adapted to receive the aerosol-generating article and at least one piercing member for piercing the nicotine powder receptacle. Preferably, such a device is re-usable. Preferably, the device also comprises a mouthpiece. The mouthpiece may be integral to the device or detachable.

As used herein, the term "aerosol-generating device" refers to a device that interacts with an aerosol-generating article to generate an aerosol that is directly inhalable into a user's lungs thorough the user's mouth.

By utilising at least one piercing member to pierce the nicotine powder receptacle the nicotine powder delivery system in accordance with the present invention provides consistent and reliable release of the nicotine powder from the receptacle. To facilitate effective delivery of the nicotine powder from the nicotine powder receptacle to the user, the at least one piercing member preferably comprises a hollow shaft portion and at least one aperture in the hollow shaft portion. When the article is received by the nicotine powder delivery device the at least one aperture is in fluid communication with the interior of the nicotine powder receptacle. In such embodiments, the airflow through the article is directed into the hollow shaft portion and to the mouth of the user.

The device may include at least one airflow inlet and at least one airflow outlet. In those embodiments in which the device comprises a mouthpiece, the at least one airflow outlet is provided in the mouthpiece.

The device according to the invention may be formed from any suitable material, such as, for example, a plastic.

The at least one piercing member may comprise a plurality of piercing elements. For example, the at least one piercing member may comprise between one and four piercing members.

The outer housing may be cylindrical in shape. In such embodiments, the outer housing may have an outer diameter of between about 9 and about 12 millimeters. In a particularly preferred embodiment, the outer housing has an outer diameter of about 10 millimeters.

Additionally, or alternatively, the outer housing preferably has an inner diameter of between about 7 and about 10 millimeters. In a particularly preferred embodiment, the outer housing has an inner diameter of about 8 millimeters. The inner diameter of the outer housing is preferably substantially the same as the outer diameter of the aerosol-generating article to provide an interference fit when the aerosol-generating article is inserted into the device.

The nicotine powder delivery system preferably has a resistance to draw of between about 25 mmWG and about 100 mmWG. In a particularly preferred embodiment, the nicotine powder delivery system has a resistance to draw of about 50 mmWG. Resistance to draw is measured in accordance with ISO 6565-2002.

The invention will now be further illustrated, by way of example only, with reference to the accompanying drawings in which.

Figure 1:
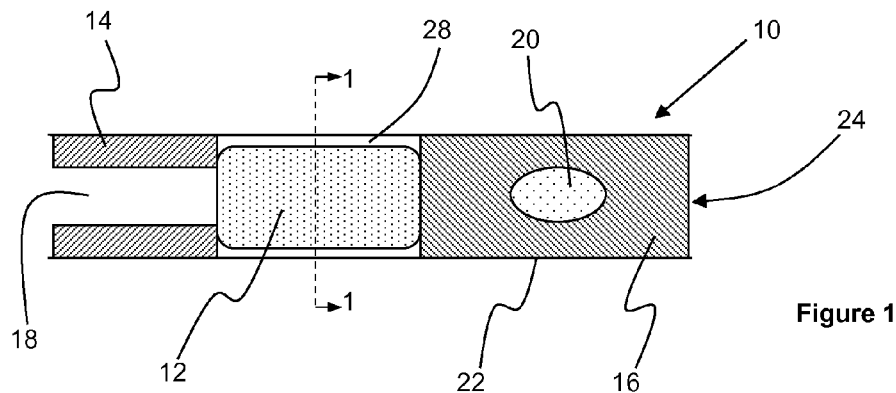
FIG. 1 shows an aerosol-generating article comprising a nicotine powder capsule in accordance with an embodiment of the present invention.

FIG. 1 shows an aerosol-generating article 10 comprising a nicotine powder capsule 12 positioned between a downstream segment 14 and an upstream segment 16. The downstream segment 14 is an annular segment comprising a hollow portion 18 for receiving a piercing member, as described in more detail below with reference to FIG. 3.

A liquid flavourant capsule 20 is provided within the upstream segment 16 and can be crushed by a user prior to using the article 10 to release the flavourant into the upstream segment 16.

An outer wrapper 22 is wrapped around the downstream segment 14, the nicotine powder capsule 12 and the upstream segment 16. An upstream end of the upstream segment 16 forms an airflow inlet 24 of the article 10.

Figure 2:
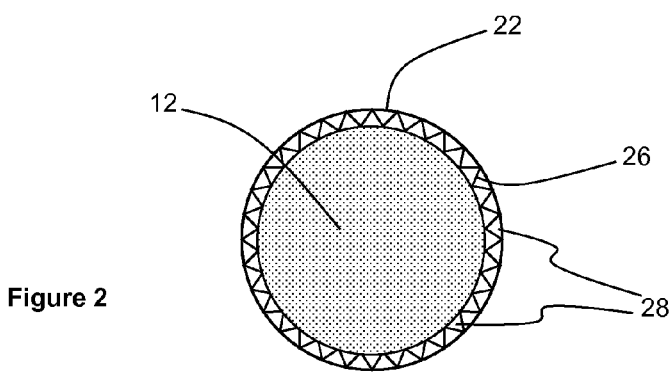
FIG. 2 shows a cross-sectional view of the article of FIG. 1 at the plane 1-1.

As shown in more detail in FIG. 2, a corrugated inner wrapper 26 is provided between the nicotine powder capsule 12 and the outer wrapper 22. The corrugations in the corrugated wrapper 26 define a plurality of airflow channels 28 in fluid communication with the airflow inlet 24 via the upstream segment 16. The plurality of airflow channels 28 allows the delivery of the flavourant from the upstream end of the article 10 to the downstream end, for delivery to the user.

Figure 3:
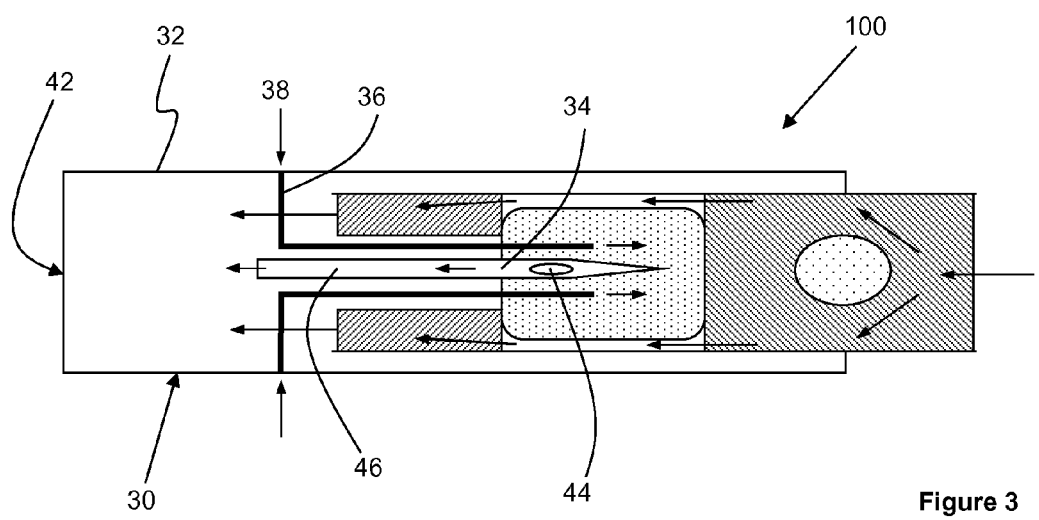
FIG. 3 shows a nicotine powder delivery system in accordance with the present invention and comprising the article of FIG. 1 received within a nicotine powder delivery device.

In use, the article 10 is inserted into a nicotine powder inhalation device 30 to form a nicotine powder delivery system 100, as shown in FIG. 3.

The inhalation device 30 comprises an outer housing 32 in which the article 10 is received. A piercing member 34 and airflow inlet channels 36 pierce the nicotine powder capsule 12 and provide fluid communication between inlet apertures 38 provided in a sidewall of the outer housing 32 and an airflow outlet 42 at a downstream end of the device 30. As illustrated by the arrows in FIG. 3, when a user draws on the downstream end of the device 30, air is drawn into the nicotine powder capsule 12 via inlet apertures 38 and airflow inlet channels 36. Nicotine particles are dispersed in the incoming air and exit the nicotine containing capsule 12 via an aperture 44 in the piercing member 34 before passing to the airflow outlet 42 via a hollow shaft portion 46 of the piercing member 34.

Also illustrated in FIG. 3 is the airflow from the airflow inlet 24 at the upstream end of the aerosol-generating article 10. In particular, when a user draws on the downstream end of the device 30, flavourant from the liquid flavourant capsule 20 becomes entrained in air flowing into the airflow inlet 24. The airflow containing the flavourant then passes through the upstream segment 16, through the airflow channels 28 defined by the corrugated inner wrapper 26, and then through the downstream segment 14 to the airflow outlet 42.

The invention claimed is:

1. An aerosol-generating article, comprising:
   a nicotine powder receptacle containing a dose of nicotine powder;
   a corrugated inner wrapper wrapped around the nicotine powder receptacle;
   an outer wrapper wrapped around the corrugated inner wrapper;
   at least one airflow inlet upstream of the nicotine powder receptacle; and
   at least one airflow outlet downstream of the nicotine powder receptacle,
   wherein corrugations in the corrugated inner wrapper define a plurality of airflow channels in fluid communication with the at least one airflow inlet and the at least one airflow outlet.

2. The aerosol-generating article according to claim 1, wherein the corrugated inner wrapper comprises a corrugated paper.

3. The aerosol-generating article according to claim 2, wherein the corrugated paper has a basis weight of at least 70 grams per square meter.

4. The aerosol-generating article according to claim 2, wherein the corrugated paper has a caliper of at least 100 micrometers.

5. The aerosol-generating article according to claim 1, wherein the nicotine powder receptacle comprises a breakable capsule.

6. The aerosol-generating article according to claim 5, wherein the breakable capsule comprises at least one of gelatine, hydroxy propyl methyl cellulose, polyethylene, polypropylene, polyurethane, fluorinated ethylene propylene, and combinations thereof.

7. The aerosol-generating article according to claim 5, wherein the breakable capsule is breakable with a crushing force of less than 5 Newtons when measured in accordance with ASTM D6175.

8. The aerosol-generating article according to claim 1, wherein the nicotine powder comprises a nicotine salt.

9. The aerosol-generating article according to claim 1, wherein the nicotine powder comprises at least one of nicotine tartrate, nicotine aspartate, nicotine lactate, nicotine glutamate, nicotine bitartrate, nicotine salicylate, nicotine fumarate, nicotine mono-pyruvate, nicotine hydrochloride, and combinations thereof.

10. The aerosol-generating article according to claim 1, further comprising a flavour delivery element.

11. The aerosol-generating article according to claim 10, wherein the flavour delivery element is upstream of the nicotine powder receptacle.

12. The aerosol-generating article according to claim 10, wherein the flavour delivery element is a breakable capsule.

13. The aerosol-generating article according to claim 10, wherein the flavour delivery element comprises a liquid flavourant or a powdered flavourant.

14. The aerosol-generating article according to claim 10, wherein the flavour delivery element is a thread impregnated with menthol.

15. A nicotine powder delivery system, comprising:
   an aerosol-generating article, comprising:
      a nicotine powder receptacle containing a dose of nicotine powder,
      a corrugated inner wrapper wrapped around the nicotine powder receptacle,
      an outer wrapper wrapped around the corrugated inner wrapper,
      at least one airflow inlet upstream of the nicotine powder receptacle, and
      at least one airflow outlet downstream of the nicotine powder receptacle,
      wherein corrugations in the corrugated inner wrapper define a plurality of airflow channels in fluid communication with the at least one airflow inlet and the at least one airflow outlet; and
   a nicotine powder inhalation device, comprising:
      an outer housing configured to receive the aerosol-generating article, and
      at least one piercing member configured to pierce the nicotine powder receptacle.

* * * * *